US008946423B2

(12) United States Patent
Ikemoto

(10) Patent No.: US 8,946,423 B2
(45) Date of Patent: Feb. 3, 2015

(54) HIGHLY SOLUBLE SALT OF PYRROLOQUINOLINE QUINONE AND METHOD FOR PRODUCING THE SAME

(75) Inventor: Kazuto Ikemoto, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/989,974

(22) PCT Filed: Nov. 25, 2011

(86) PCT No.: PCT/JP2011/077213

§ 371 (c)(1), (2), (4) Date: Jun. 7, 2013

(87) PCT Pub. No.: WO2012/070649

PCT Pub. Date: May 31, 2012

(65) Prior Publication Data

US 2013/0253001 A1 Sep. 26, 2013

(30) Foreign Application Priority Data

Nov. 26, 2010 (JP) ................................ 2010-263548

(51) Int. Cl.
*C07D 471/04* (2006.01)
*A61K 31/475* (2006.01)

(52) U.S. Cl.
CPC ............ *C07D 471/04* (2013.01); *A61K 31/475* (2013.01)
USPC ............................................ 546/84; 514/292

(58) Field of Classification Search
USPC ............................................ 514/292; 546/84
See application file for complete search history.

(56) References Cited

U.S. PATENT DOCUMENTS

| | | | | |
|---|---|---|---|---|
| 5,460,819 | A * | 10/1995 | Gallop et al. | 514/292 |
| 2010/0261749 | A1 * | 10/2010 | Kamimura et al. | 514/292 |
| 2011/0313164 | A1 | 12/2011 | Zhong et al. | |
| 2014/0127288 | A1 | 5/2014 | Ikemoto | |

FOREIGN PATENT DOCUMENTS

| | | |
|---|---|---|
| CN | 101851234 | 10/2010 |
| CN | 101885752 | 11/2010 |
| JP | 62 246575 | 10/1987 |
| JP | 63 156724 | 6/1988 |
| JP | 2 53477 | 2/1990 |
| JP | 3 112912 | 5/1991 |
| JP | 7 113024 | 5/1995 |
| JP | 2751183 | 5/1998 |
| WO | WO 94/01142 | 1/1994 |

OTHER PUBLICATIONS

Smith; Journal of Chromatography A, 876 (2000) 193-199.*
Itoh; Yukagaku, 1986, 35, 91-95.*
Berge, S. et al., "Pharmaceutical Salts," Journal of Pharmaceutical Sciences, vol. 66, No. 1, pp. 1 to 19, (Jan. 1977), XP000562636.
"A new redox-cofactor vitamin for mammals," Nature Publishing Group, vol. 422, p. 832, (Apr. 24, 2003).
"Total Synthesis of the Quinonoid Alcohol Dehydrogenase Coenzyme (1) of Methylotrophic Bacteria,", Journal of American Chemical Society, vol. 103, pp. 5599 to 5600, (1981).
"Molecular and Crystal Structure of PQQ (Methoxatin), a Novel Coenzyme of Quinoproteins: Extensive Stacking Character and Metal Ion Interaction, " Journal of American Chemical Society, vol. 111, pp. 6822 to 6828, (1989).
Itoh, S. et al., "Reaction of Reduced PQQ (PQQH2) and Molecular Oxygen," The Chemical Society of Japan, vol. 59, pp. 1911 to 1914, (1986).
Ouchi, A. et al., "Kinetic Study of the Antioxidant Activity of Pyrroloquinolinequinol (PQQH2, a Reduced Form of Pyrroloquinolinequinonone) in Micellar Solution," Journal of Agricultural and Food Chemistry, vol. 57, No. 2, pp. 450 to 456, (2009).
International Search Report Issued Feb. 14, 2012 in PCT/JP11/77213 Filed Nov. 25, 2011.
U.S. Appl. No. 13/261,856, filed May 14, 2014, Ikemoto.

* cited by examiner

*Primary Examiner* — John Mabry
*Assistant Examiner* — Daniel Carcanague
(74) *Attorney, Agent, or Firm* — Oblon, Spivak, McClelland, Maier & Neustadt, L.L.P.

(57) ABSTRACT

An object of the present invention is to provide a salt of pyrroloquinoline quinone having a high solubility in water and in an organic solvent and a method for producing the same. According to the present invention, there are provided an ammonium salt of pyrroloquinoline quinone having a high solubility in water and in an organic solvent, consisting of a pyrroloquinoline quinone ion and an ammonium salt having a hydroxyl group.

7 Claims, No Drawings

HIGHLY SOLUBLE SALT OF PYRROLOQUINOLINE QUINONE AND METHOD FOR PRODUCING THE SAME

CROSS-REFERENCE TO RELATED APPLICATION

This application enjoys the benefit of priority to earlier Japanese Patent Application No. 2010-263548 filed on Nov. 26, 2010, the disclosure of which is incorporated herein by reference in its entirety.

TECHNICAL FIELD

This invention relates to a highly soluble salt of pyrroloquinoline quinone and a method for producing the same.

BACKGROUND ART

Pyrroloquinoline quinone (hereinafter sometimes referred to as "PQQ") has been proposed as a possible new vitamin (see, for example, Non-patent document 1), and has attracted much attention as a useful material for dietary supplements, cosmetics, etc. Moreover, PQQ is present not only in bacteria but also in eukaryotic molds and yeasts and plays an important role as a cofactor. Also, PQQ has been found to have many physiological activities such as cell growth-promoting activity, anti-cataract activity, hepatic disease-preventing and therapeutic activity, wound healing activity, antiallergic activity, reverse transcriptase-inhibiting activity and glyoxalase I-inhibiting activity—anticancer activity, nerve fiber regeneration, and the like.

PQQ can be obtained as an alkali metal salt form by subjecting a product obtained by methodologies such as organic chemical syntheses (Non-patent document 2) or fermentation processes (Patent document 1) to chromatography, concentrating the PQQ fraction in the effluent and adding an organic solvent to the fraction followed by crystallization (Patent document 2). This alkali metal salt of PQQ, which has been known as a water soluble substance, in fact has low solubility in water, and PQQ in the free form has lower solubility in water. Moreover, the solubility of the alkali metal salt of PQQ in alcohol is even lower than in water. The alkali metal salt of PQQ has a low solubility because of the presence of molecular interactions due to hydrogen bonds and ionic bonds (Non-patent document 3). This is why it is difficult to prepare an aqueous solution having a high concentration of an alkali metal salt of PQQ and even more difficult to provide a solution of the alkali metal salt of PQQ in an organic solvent.

Solutions of PQQ in water and in ethanol, however, are most commonly used when provided for use in the food and pharmaceutical fields, so that PQQ is required to be easily dissolved at a high concentration in such a solvent and to remain unprecipitated. Also in separation and purification of PQQ, its low solubility entails disadvantages of requiring large amounts of a solvent (water in particular) for dissolving it and thus large equipment, and producing large amounts of waste water. Moreover, PQQ is required to be soluble in a solvent having a higher vapor pressure because water needs much heat to evaporate, which results in higher costs of fuel. From these, there is a need for PQQ having an increased solubility.

Furthermore, PQQ has a quinone structure, which is readily reduced (Non-patent document 4), and this reduced PQQ has also attracted attention by its functions (Non-patent document 5).

PRIOR ART DOCUMENTS

Patent document

Patent document 1: Japanese Patent No. 2751183

Patent document 2: Japanese Patent Laid-open Publication No. 07-113024

Non-Patent Document

Non-patent document 1: Nature, vol. 422, 24, Apr., 2003, p. 832

Non-patent document 2: JACS, vol. 103, p. 5599-5600 (1981)

Non-patent document 3: JACS, vol. 111, p. 6822-6828 (1989)

Non-patent document 4: Bull. Chem. Soc. Jpn., vol. 59, p. 1911-1914 (1986)

Non-patent document 5: J. Agric. Food Chem., vol. 57, p. 450-456 (2009)

SUMMARY OF THE INVENTION

An object of the present invention is to provide a salt of pyrroloquinoline quinone which has high solubility in water and in organic solvents, and to provide a method for producing the same.

The present inventors have found that a salt of pyrroloquinoline quinone having a high solubility in water and in an organic solvent can be prepared by forming a salt from a pyrroloquinoline quinone ion and an ammonium ion. The present inventors have also demonstrated that an ammonium salt of reduced pyrroloquinoline quinone corresponding to the obtained ammonium salt of oxidized pyrroloquinoline quinone can be prepared. The present invention is based on these discoveries.

According to the present invention, the following inventions are provided:

<1>An ammonium salt of oxidized pyrroloquinoline quinone of formula (1)

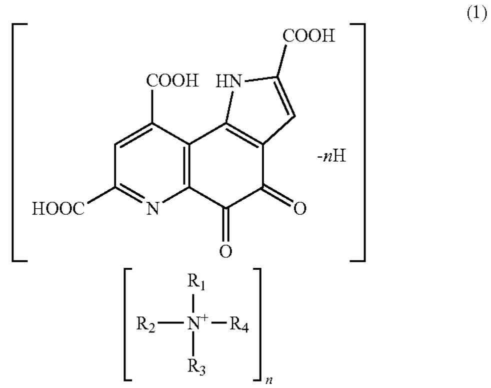

wherein $R_1$ represents a hydroxyalkyl group having one to four carbon atoms, $R_2$ and $R_3$ each represent a hydroxyalkyl or alkyl group having one to four carbon atoms, $R_4$ represents hydrogen or a hydroxyalkyl or alkyl group having one to four carbon atoms, and n is one to three;

<2> An ammonium salt of reduced pyrroloquinoline quinone of formula (2)

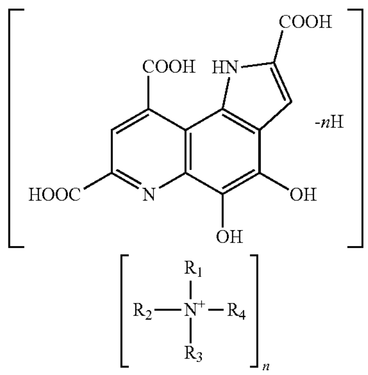

wherein $R_1$ represents a hydroxyalkyl group having one to four carbon atoms, $R_2$ and $R_3$ each represent a hydroxyalkyl or alkyl group having one to four carbon atoms, $R_4$ represents hydrogen or a hydroxyalkyl or alkyl group having one to four carbon atoms, and n is one to three;

<3> The ammonium salt of oxidized pyrroloquinoline quinone of <1>, wherein $R_1$ represents a hydroxyethyl group, and $R_2$, $R_3$ and $R_4$ each represent a methyl group;

<4> The ammonium salt of reduced pyrroloquinoline quinone of <2>, wherein $R_1$ represents a hydroxyethyl group, and $R_2$, $R_3$ and $R_4$ each represent a methyl group;

<5> A composition comprising the ammonium salt of oxidized pyrroloquinoline quinone of <1> or <3> and a reducing agent;

<6> The composition of <5>, wherein the weight ratio of the reducing agent to the ammonium salt of oxidized pyrroloquinoline quinone is in a range of 0.01 to 100;

<7> A composition comprising the ammonium salt of oxidized pyrroloquinoline quinone of <1> or <3> and the ammonium salt of reduced pyrroloquinoline quinone of <2> or <4>;

<8> A composition comprising oxidized or reduced pyrroloquinoline quinone or an alkali metal salt thereof and an ammonium salt;

<9> The composition of <8>, wherein the ammonium salt is a choline salt, and the weight ratio of the choline salt to the oxidized or reduced pyrroloquinoline quinone or the alkali metal salt thereof is in a range of 0.01 to 2000;

<10> A method for producing an ammonium salt of the oxidized pyrroloquinoline quinone represented by formula (1) of <1> or that of the reduced pyrroloquinoline quinone represented by formula (2) of <2>, comprising the steps of: subjecting an alkali metal salt of the oxidized or reduced pyrroloquinoline quinone to acidic conditions; and mixing it with ammonium hydroxide;

<11> The method of <10>, wherein ammonium hydroxide is choline hydroxide, and the salt produced is a choline salt of the oxidized or reduced pyrroloquinoline quinone.

According to the present invention, a highly soluble salt of pyrroloquinoline quinone can be provided. Accordingly, there can be provided aqueous and alcohol solutions containing a high concentration of PQQ, for example, homogeneous and high concentration PQQ solutions effective for use in pharmaceutical products, food products and feed. Also, according to the present invention, a choline salt of pyrroloquinoline quinone can be provided. This enables simultaneous intake of PQQ and a choline component which is important as a nutritional component and has functions to improve liver, lipid metabolism, and neurological functions.

DETAILED DESCRIPTION OF THE INVENTION

The salt provided according to the present invention is a salt of an ammonium having a hydroxyl group and pyrroloquinoline quinone. The solubility of pyrroloquinoline quinone can be significantly improved by forming a salt of the ammonium and pyrroloquinoline quinone. The pyrroloquinoline quinone generally refers to oxidized pyrroloquinoline quinone (in the free form) of formula (5) below having a quinone structure, and reduced pyrroloquinoline quinone (in the free form) of formula (6) having a hydroquinoline structure which is a reduced quinone structure can also be produced.

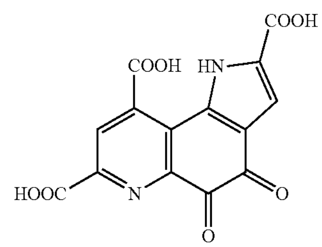

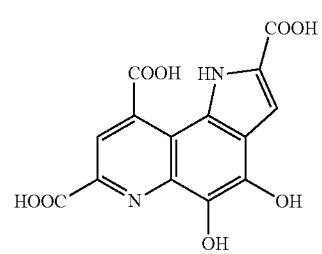

Although the term "pyrroloquinoline quinone" (PQQ) as used herein refers to oxidized pyrroloquinoline quinone (oxidized PQQ) unless explicitly indicated otherwise, there are provided a salt of oxidized pyrroloquinoline quinone and a salt of reduced pyrroloquinoline quinone according to the present invention.

Specifically, according to the present invention, there are provided an ammonium salt of oxidized pyrroloquinoline quinone having a molar ratio of the oxidized pyrroloquinoline quinone ion to the ammonium ion in formula (1) in a range of 1:1 to 1:3, and an ammonium salt of reduced pyrroloquinoline quinone having a molar ratio of the reduced pyrroloquinoline quinone ion and the ammonium ion in formula (2) in a range of 1:1 to 1:3. In formulae (1) and (2), "-nH" means that the oxidized or reduced pyrroloquinoline quinone is an oxidized or reduced pyrroloquinoline quinone ion having a valence corresponding to the number of ammonium ions present. The molar ratio of the oxidized pyrroloquinoline quinone ion to the ammonium ion in formula (1) is in a range of preferably 1:1.4 to 1:3 (n=1.4 to 3), more preferably 1:1.9 to 1:3 (n=1.9 to 3), particularly preferably 1:2 to 1:3 (n=2 to 3), and most preferably 1:2.4 to 1:3 (n=2.4 to 3). The molar ratio of the reduced pyrroloquinoline quinone ion to the ammonium ion in formula (2) is in a range of preferably 1:1.4 to 1:3 (n=1.4 to 3), more preferably 1:1.9 to 1:3 (n=1.9 to 3), particularly preferably 1:2 to 1:3 (n=2 to 3), and most preferably 1:2.4 to 1:3 (n=2.4 to 3).

The hydroxyalkyl group includes, for example, hydroxyethyl group, hydroxypropyl group, and hydroxybutyl group.

Among the salts according to the present invention, more preferred are a choline salt of oxidized pyrroloquinoline quinone having a molar ratio of the oxidized pyrroloquinoline quinone ion to the trimethylhydroxyethylammonium ion (choline ion) in formula (1) wherein $R_1$ represents 2-hydroxyethyl group, and $R_2$, $R_3$ and $R_4$ each represent a methyl group in a range of 1:1 to 1:3, and a choline salt of reduced pyrroloquinoline quinone having a molar ratio of the reduced pyrroloquinoline quinone ion to the choline ion in formula (2) in a range of 1:1 to 1:3. The choline salt of oxidized pyrroloquinoline quinone and the choline salt of reduced pyrroloquinoline quinone mentioned above can be represented by formula (3) and formula (4), respectively.

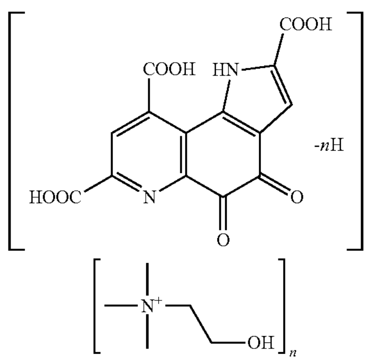

(3)

wherein, n is one to three.

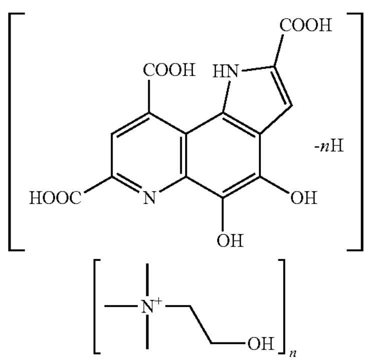

(4)

wherein, n is one to three.

In formulae (3) and (4), "-nH" means that the oxidized or reduced pyrroloquinoline quinone is an oxidized or reduced pyrroloquinoline quinone ion having a valence corresponding to the number of choline ions present. Also, the molar ratio of the oxidized pyrroloquinoline quinone ion to the choline ion in formula (3) is in a range of preferably 1:1.4 to 1:3 (n=1.4 to 3), more preferably 1:1.9 to 1:3 (n=1.9 to 3), particularly preferably 1:2 to 1:3 (n=2 to 3), and most preferably 1:2.4 to 1:3 (n=2.4 to 3). The molar ratio of the reduced pyrroloquinoline quinone ion to the choline ion in the formula (4) is in a range of preferably 1:1.4 to 1:3 (n=1.4 to 3), more preferably 1:1.9 to 1:3 (n=1.9 to 3), particularly preferably 1:2 to 1:3 (n=2 to 3), and most preferably 1:2.4 to 1:3 (n=2.4 to 3).

The term "alkyl" as used herein refers to a straight, branched-chain or cyclic alkyl. The alkyl groups having one to four carbon atoms include methyl, ethyl, n-propyl, i-propyl, n-butyl, i-butyl, t-butyl, and the like.

The ammonium salt of PQQ according to the present invention can be prepared by reacting PQQ in the free form or an alkali metal salt thereof with an ammonium. In the reaction, the number of the ammonium moieties added can be determined by the molar ratio or pH.

The PQQ used may be in the free form or in the form of an alkali metal salt including sodium, potassium, lithium, cesium, and rubidium salts, and used singly or in combination thereof. More preferred are sodium and potassium salts, and among them, the most available sodium salt is particularly preferred. Salt(s) of carboxylic acid(s) may be any one of mono-salt, di-salts and tri-salts, and particularly preferably disodium salts. These raw materials can be produced by organic chemical syntheses and fermentation processes. The salt of pyrroloquinoline quinone used as a raw material may be crystalline or amorphous. Moreover, it may have some impurities.

The ammonium used is a quarternary ammonium salt having a hydroxyl group, and an ammonium salt of a tertiary amine having a hydroxyl group. Specific examples of the ammonium salts having a hydroxyl group include trimethylhydroxyethylammonium salt (choline salt), trimethylhydroxypropylammonium salt, trimethylhydroxybutylammonium salt, triethylhydroxyethylammonium salt, triethylhydroxypropylammonium salt, di(hydroxyethyl)dimethylammonium salt, di(hydroxypropyl)dimethylammonium salt, tri(hydroxyethyl)methylammonium salt, tri(hydroxypropyl)methylammonium salt, trihydroxyethylammonium salt, trihydroxypropylammonium salt, dimethyl(hydroxyethyl)ammonium salt, dimethyl(hydroxypropyl)ammonium salt, dihydroxyethylmethylammonium salt, dihydroxypropylmethylammonium salt, and the like.

The ammonium salt that can be used includes ammonium hydroxide, ammonium carbonate, ammonium chloride, ammonium bromide, ammonium iodide and the like, and more preferred is ammonium hydroxide.

When an ammonium salt of PQQ is prepared in an aqueous solution, the pH of the aqueous solution may be 2 to 10. The ammonium salt of PQQ is often obtained at a pH of 2 to 5 for two ammonium salts per PQQ molecule, and at a higher pH (pH 5 or more) for three ammonium salts per PQQ molecule. Depending on the pH value, the obtained salt may have a composition not in a ratio of whole numbers but a nonstoichiometric composition. That is, the composition (molar ratio) of the salt according to the present invention is not necessary in a ratio of whole numbers, and the salt may be obtained as a nonstoichiometric substance. This pH is used as a rough measure in the preparation of the ammonium salt of PQQ, and the obtained substance may vary under the influence of coexisting salts and the like.

The reaction can be carried out in either water or an organic solvent. The reaction temperature is not specifically limited, and the temperatures of −20° C. to 140° C., and more preferably −10° C. to 90° C. are used. The reaction is preferably carried out for 10 minutes to 7 days, although the needed reaction time varies depending on, for example, the mixing speed, stirring, temperature, and concentration of the reaction. As the reaction proceeds, the solubility of PQQ in water and in alcohol is increased. Besides this method, an ammonium salt of PQQ can be obtained by using ion exchange resins to exchange an alkali metal salt of PQQ for the ammonium salt of PQQ.

Also, an alkali metal salt of PQQ, which is readily available as a raw material, can be subjected to strongly acidic conditions at pH of approximately 1 to obtain the free form as a precipitate. The precipitate is then filtered and subjected to the reaction with an ammonium hydroxide to obtain the ammonium salt of PQQ. The ammonium hydroxide can be mixed in an amount of one to three moles per mole of the PQQ in the free form.

The method for adjusting the pH can include adding an acid or alkali. The acid or alkali may be inorganic or organic. The ammonium salt formed in an aqueous or organic solvent can be obtained by drying, concentration, reduction in the temperature, addition of a poor solvent, salting out, and change in the pH. As a solvent for dissolving the ammonium salt of PQQ, polar solvents such as water, methanol, ethanol, acetonitrile, isopropanol, glycerin, propylene glycol, methoxyethanol, methoxypropanol, dimethyl sulfoxide, acetone, dimethylformamide, dimethylacetamide, methylpyrrolidone. More preferred are water, ethanol, methanol, and isopropanol which have low toxicity even when they are included. This solution may be subjected to operations for lowering the solubility, such as cooling, concentration, addition of a poor solvent, and salting out. It is necessary to vary the poor solvent depending on the solvent used, and hexane, diethyl ether, and cyclohexane are easily used.

In the present invention, it does not matter even if an alkali metal remains. The ammonium salt according to the present invention may be a mixed salt of an ammonium salt and an alkali metal salt. The higher the number of the ammonium moieties added in the ammonium salt of PQQ, the higher effect of increasing the solubility.

A specific preferred method for producing a choline salt of PQQ that is readily available, has low toxicity and is highly safe will now be described. The production method comprising converting PQQ in the alkali metal salt form into the free form, and subsequently into the choline salt form needs no special equipment, and can be readily carried out. The alkali metal salt of PQQ is dissolved in water. The pH of the aqueous solution is desirably 3 to 13, and more preferably 5 to 12. An alkaline solution may be added for adjusting the pH of the aqueous solution. The aqueous solution may be at a temperature of 0 to 140° C. To this solution, an acid is added to adjust the pH to 1.8 or less, and solid PQQ in the free form is thereby precipitated. This solid was separated by methods such as filtration and centrifugation.

A choline salt of PQQ can be formed by reacting this PQQ in the free form with choline hydroxide in water or in an organic solvent. The reaction time is not specifically limited, but the reaction can be carried out for five minutes to about one week. Only a short time is required on a small scale, while a longer time on a large scale. Then, the reaction may be performed at a temperature in a range of −20° C. to 140° C., and preferably in a range of 0° C. to 80° C. The reacted liquid can be subjected to concentration to dryness or recrystallization to leave a choline salt of PQQ as a solid. For the purpose of this invention, the salt is not necessary a solid. The recrystallization may be carried out in water or in a solvent. The resultant solid may be dried under normal or reduced pressure.

As sources of the choline ion, choline chloride, choline bromide, choline iodide, choline carbonate, choline bicarbonate, choline hydroxide, choline acetate, choline tartrate, choline lactate, choline phosphate and the like can be used. In the case of the reaction, preferred is choline hydroxide, and in other cases, preferred is choline chloride.

The choline salt of PQQ according to the present invention may be used without isolation. Moreover, for the purpose of this invention, PQQ in the free form or in the alkali metal salt form may be used in a mixture with a choline salt, in which case, the weight ratio of the choline salt to PQQ is preferably 0.01 to 2000, and more preferably 0.01 to 100.

That is, according to the present invention, there is provided a composition comprising oxidized or reduced pyrroloquinoline quinone in the free form or an alkali metal salt thereof and an ammonium salt. In this composition, the weight ratio of the ammonium salt to the oxidized or reduced pyrroloquinoline quinone in the free form or the alkali metal salt thereof can be in a range of 0.01 to 2000, and preferably in a range of 0.01 to 100. When the ammonium salt is a choline salt in this composition, the weight ratio of the choline salt to the oxidized or reduced pyrroloquinoline quinone in the free form or the alkali metal salt thereof can be in a range of 0.01 to 2000, and preferably in a range of 0.01 to 100.

As mentioned before, according to the present invention, an ammonium salt of reduced PQQ is provided in addition to an ammonium salt of oxidized PQQ. The ammonium salt of reduced PQQ according to the present invention can be easily obtained by forming the ammonium salt of oxidized PQQ followed by reduction reaction. Alternatively, the ammonium salt of reduced PQQ can also be obtained by reacting non-dissolved reduced PQQ in the free form or an alkali metal salt thereof with an ammonium ion. The reduced PQQ has lower solubility than the oxidized PQQ does, and is more easily precipitated. The preparation of the ammonium salt of reduced PQQ through reaction of reduced PQQ in the free form or an alkali metal salt thereof with an ammonium ion can be made according to the preparation procedure for the ammonium salt of oxidized PQQ as mentioned above.

The reduction reaction may be either catalytic reduction or reagent reduction and not particularly limited. The catalytic reduction can be carried out by selecting conditions such as catalysts, for example, noble metal catalysts and Raney catalysts. As an agent for reagent reduction, common substances such as ascorbic acid, cysteine, borohydride, NADPH, hydrosulfite, hydrazine and the like can be used. More preferably suitable are ascorbic acid, cysteine, and NADPH that have low biotoxicity. These substances can be used singly as well as in combination thereof. A mixture of a choline salt and a reducing agent can also be provided for forming this choline salt in the reduced form. The weight ratio of the reducing agent to the choline salt of PQQ is preferably 0.01 to 100, and more preferably 0.1 to 100. The reduced form has great radical-scavenging ability, which is useful for measures against damages thought to be caused by active oxygen.

That is, according to the present invention, there is provided a composition comprising an ammonium salt of oxidized PQQ and a reducing agent. In this composition, the weight ratio of the reducing agent to the ammonium salt of oxidized PQQ can be in a range of 0.01 to 100, and preferably in a range of 0.1 to 100. When the ammonium salt of oxidized PQQ is a choline salt of oxidized PQQ in the composition above, the weight ratio of the reducing agent to the choline salt can be in a range of 0.01 to 100, and preferably in a range of 0.1 to 100.

Depending on the amount of the reducing agent added to the ammonium salt of oxidized PQQ, the salt of oxidized PQQ and the salt of reduced PQQ may be present together in the composition. Also, mixing of reduced PQQ with oxidized PQQ or oxidation of reduced PQQ by an oxidizing agent or oxygen in the air may make the salt of oxidized PQQ and the salt of reduced PQQ present together in the composition. Such a composition also constitutes an aspect of the present invention. That is, according to the present invention, there is provided a composition comprising an ammonium salt of oxidized PQQ according to the present invention and an ammonium salt of reduced PQQ according to the present invention. A more specific embodiment of the present invention provides a composition comprising a choline salt of oxidized PQQ according to the present invention and a choline salt of reduced PQQ according to the present invention.

The ammonium salt of PQQ according to the present invention, which is expected to be used for various industries due to its high solubility in water and in an organic solvent, can be used as an active ingredient in medicines or functional foods, for example. That is, these medicines or functional foods can be provided in forms such as topical dermatological agents, injections, oral agents and suppositories, or forms such as daily foods and drinks, nutrition-enriched diets and various hospital diets. In addition, the additive used in the preparation may include liquids such as water and sugars such as fructose and glucose, oils such as peanut oil, soybean oil and olive oil, and glycols such as polyethylene glycol and polypropylene glycol. Examples of excipients for solid preparations such as tablets, capsules and granules may include sugars such as lactose, sucrose and mannitol, lubricants may include kaolin, talc and magnesium stearate, disintegrants may include starch and sodium alginate, binders may include polyvinyl alcohol, cellulose and gelatin, surfactants may include fatty acid ester, and plasticizers may include glycerin. The examples are not limited by those cited above. Solubility enhancing agents and fillers may be added if necessary.

The ammonium salt of PQQ according to the present invention may be used alone or in combination of other materials. Examples of the material that may be used in combination include, but not limited thereto, vitamins such as vitamin B, vitamin C and vitamin E, amino acids, astaxanthin, carotenoids such as α-carotene and β-carotene, ω-3 fatty acids such as docosahexaenoic acid and eicosapentaenoic acid, and ω-6 fatty acids such as arachidonic acid.

EXAMPLES

The present invention will now be described in more detail with reference to the following examples and comparative examples, but is not intended to be limited thereto.

Unless otherwise noted, the reagents used were available from Wako Pure Chemical Industries, Ltd. Analysis of ultraviolet and visible absorption spectra was carried out with a HITACHI U-2000 spectrometer.

(HPLC Analysis)

The HPLC analysis was carried out using a high performance liquid chromatography LC-20A from SHIMADZU CORPORATION equipped with a column: YMC-Pack ODS-TMS (5 μm) 150×4.6 mm I.D., with 100 mM $CH_3COOH$/100 mM $CH_3COONH_4$ (30/70, pH 5.1) as an eluent and detection at 260 nm.

(Ion Chromatography Analysis)

An ion chromatograph DX-120 from DIONEX equipped with a CS12A column and an eluent CS12A for DIONEX cation analysis from KANTO CHEMICAL CO., INC. were used.

(NMR Analysis)

A 500 MHz JEOL JNM-ECA 500 NMR spectrometer was used. (DMSO-$d_6$: 2.529 ppm reference), and for 13C-NMR (DMSO-$d_6$: 39.5 ppm reference) were used.

Example 1

Synthesis of Disodium Salt of PQQ and Preparation of Monocholine Salt of PQQ Synthesis of Disodium Salt of PQQ A culture solution obtained by culturing Hyphomicrobium denitrificans DSM1869 was centrifuged, and the bacterial cells were removed to give a culture supernatant containing PQQ, according to Example 1 in Japanese Patent No. 2692167. Here, this bacterial strain is available from DSM (Deutsche Sammlung von Mikroorganismen (German Collection of Microorganisms and Cell Cultures)).

This culture supernatant was passed through a Sephadex G-10 column (from Pharmacia), on which PQQ was adsorbed. The adsorbed PQQ was eluted with an aqueous NaCl solution to give an aqueous PQQ solution having a pH of 7.5. To the PQQ solution was added NaCl so that the resultant concentration is 60 g/L. The solution was cooled to give a solid. The resultant solid was dissolved in water, and the PQQ had a purity of 99.0% or more as indicated by UV absorption on high performance liquid chromatography. This solid was dissolved in ion-exchanged water to provide 800 g of a solution containing 10 g/L of PQQ. The pH of the solution was adjusted to 3.5 by the addition of hydrochloric acid and then 200 mL of ethanol were added to the solution. At this time, a red solid was precipitated. After being stirred at room temperature for five hours, the solution was allowed to stand at 5° C. for 24 hours, resulting in precipitation of a solid. The solid was recovered through continuous centrifugation, and dried under reduced pressure at 50° C. to yield a disodium salt of PQQ.

Formation of PQQ in the Free Form

To 198 g of water were added 2 g of the disodium salt obtained as above, and the solution was adjusted to pH 9 with NaOH. To this solution, 7.7 g of a solution obtained by subjecting concentrated hydrochloric acid (from Wako Pure Chemical Industries, Ltd.) to dilution by 50% were added while stirring to adjust the pH to 0.9. After the mixture was stirred for 30 minutes, the precipitated solid was filtered, washed with water and isopropanol, and then dried under reduced pressure at 50° C. overnight. The PQQ in the free form was collected as red crystals with a yield of 1.6 g. $^1H$- and $^{13}C$-NMR spectra were measured for the produced PQQ in free form in DMSO-$d_6$ at room temperature. The results showed the $^1H$-NMR chemical shifts at 7.21 and 8.60 ppm and the $^{13}C$-NMR chemical shifts at 113.5, 124.5, 126.4, 127.6, 129.2, 134.3, 136.3, 146.8, 148.7, 160.9, 164.9, 168.7, 173.3, and 178.0 ppm.

Preparation of a Monocholine Salt of PQQ

The PQQ in the free form obtained above was used. A 0.62 g aliquot of the PQQ in the free form was suspended in water. To the suspension were added 1.39 g of an aqueous solution of choline hydroxide (48 to 50%) from Tokyo Chemical Industry Co., Ltd. The mixture became a homogeneous solution, and the solution had a pH of 9.4. To the solution were added 10 g of choline chloride, and no precipitation occurred. Addition of hydrochloric acid to this solution caused a solid to precipitate at a pH of 4 or less, and the solution eventually had a pH of 3.5. This solution was cooled to 4° C., and after one hour, centrifuged to yield a solid. This solid was washed with isopropanol three times, and dried under reduced pressure overnight to yield 0.64 g of red power.

A 0.15 g aliquot of this solid was dissolved in 0.8 g of DMSO-$d_6$, and $^1H$- and $^{13}C$-NMR spectra were measured for the resultant solution using a 500 MHz JEOL JNM-ECA 500 NMR spectrometer at room temperature. The results showed the $^1$H-NMR chemical shifts at 3.15, 3.44 (t), 3.87 (d), 7.15, and 8.64 ppm (DMSO-$d_6$: 2.529 ppm reference), and the $^{13}$C-NMR chemical shifts at 53.3, 55.3, 67.1, 114.0, 123.0, 126.0, 127.8, 130.8, 137.6, 144.6, 146.6, 147.9, 161.5, 165.7, 167.0, 173.5, and 179.9 ppm (DMSO-d6: 39.5 ppm reference). The results of $^1$H-NMR showed chemical shifts at 3.15, 3.44, and 3.87 ppm derived from choline and at 7.15, and 8.64 ppm derived from PQQ. This integration ratio showed that the molar ratio of choline and PQQ present was 1:1.

The $^{13}$C-NMR spectrum showed peaks of chemical shifts at 53.3, 55.3, and 67.1 ppm for the carbons of choline, and the other peaks at almost the same chemical shifts as those for PQQ in the free form from Example 1, which demonstrated that the red powder obtained was a monocholine salt of PQQ.

Example 2

Preparation of 1.4 Choline Salt of PQQ

PQQ in the free form similar to that in Example 1 was used. A 0.47 g aliquot of the PQQ in the free form was suspended in 100 ml of isopropanol. To the suspension were added 0.98 g of an aqueous solution of choline hydroxide (48 to 50%) from Tokyo Chemical Industry Co., Ltd. As the reaction proceeded, the suspension turned into a solution. The solvent was removed from this solution in a 300 ml eggplant-shaped flask using an evaporator, and the residue was washed with hexane, and dried to yield 0.97 g of a solid. The solid obtained was soluble in ethanol, and the ratio of choline to PQQ was approximately 1.4. That is, the molar ratio of PQQ to choline was approximately 1:1.4, indicating that the solid was a non-stoichiometric choline salt of PQQ.

Example 3

Preparation of Dicholine Salt of PQQ

A 1.20 g aliquot of PQQ in the free form similar to that in Example 1 was suspended in 100 ml of water. To this suspension were added approximately 1.8 g of an aqueous solution of choline hydroxide (48 to 50%) from Tokyo Chemical Industry Co., Ltd. to adjust the pH of the mixture to 3.2 over 30 minutes. The solvent was removed from this solution in a 300 ml eggplant-shaped flask using an evaporator. The obtained solid was dissolved in a mixed solvent of ethanol and isopropanol, and hexane was added to the solution to precipitate a solid. The supernatant liquid was removed through decantation to yield a solid. This solid was dried under reduced pressure to yield 2 g of the solid. This solid was diluted to a concentration of 0.025 mM, and the ultraviolet-visible absorption spectrum (at 220 to 700 nm) was measured for the diluted solution, which spectrum was the same as that for the sodium salt in the oxidized form. The structure of PQQ was maintained. LC analysis and ion chromatography analysis showed that the molar ratio of PQQ to choline was 1:1.9, indicating that the solid was a dicholine salt of PQQ.

The result of $^1$H-NMR of this choline salt in DMSO-$d_6$ showed chemical shifts at 3.15, 3.44, and 3.88 ppm derived from choline and at 6.59, and 8.21 ppm derived from PQQ. The integration ratio was consistent with the ratio mentioned above.

Example 4

Preparation of 2.4 Choline Salt of PQQ

PQQ in the free form similar to that in Example 1 was used. A 1.16 g aliquot of the PQQ in the free form was suspended in 25 ml of water. To this suspension were added approximately 2.1 g of an aqueous solution of choline hydroxide (48 to 50%) from Tokyo Chemical Industry Co., Ltd. followed by the addition of hydrochloric acid to adjust the pH of the mixture to 7.5 over 30 minutes. The solvent was removed from this solution in a 300 ml eggplant-shaped flask using an evaporator, and ethanol and hexane were added to the residue to precipitate a solid. The supernatant liquid was removed through decantation to yield a solid. This solid was dried under reduced pressure to yield 2.3 g of the solid. This solid can be dissolved in acetonitrile, isopropanol, and dimethyl sulfoxide. LC analysis and ion chromatography analysis showed that the molar ratio of PQQ to choline was 1:2.4, indicating that the solid was a nonstoichiometric choline salt of PQQ.

The result of $^1$H-NMR of this choline salt in DMSO-$d_6$ showed chemical shifts at 3.20, 3.51, and 3.90 ppm derived from choline and at 6.82, and 8.38 ppm derived from PQQ. The integration ratio was consistent with the ratio mentioned above.

Example 5

Preparation of Tricholine Salt of PQQ

PQQ in the free form similar to that in Example 1 was used. A 0.34 g aliquot of the PQQ in the free form was suspended in 25 ml of water. To this suspension were added approximately 0.75 g of an aqueous solution of choline hydroxide (48 to 50%) from Tokyo Chemical Industry Co., Ltd. to adjust the pH of the mixture to 9. After overnight stirring, the solvent was removed from this mixture in a 300 ml eggplant-shaped flask using an evaporator. The residue was washed with hexane to yield a solid. This solid was dried under reduced pressure to yield 0.67 g of the solid. LC analysis and ion chromatography analysis showed that the molar ratio of PQQ to choline was 1:3, indicating that the solid was a tricholine salt of PQQ.

The result of $^1$H-NMR of this choline salt in DMSO-$d_6$ showed chemical shifts at 3.15, 3.44, and 3.87 ppm derived from choline and at 6.60, and 8.22 ppm derived from PQQ. The integration ratio was consistent with the ratio mentioned above.

Examples 6 to 15 and Comparative Examples 1 and 2

Dissolution Test

The disodium salt of PQQ obtained by the method as described in Example 1 was used. Moreover, a choline salt from Example 1 was used as a monocholine salt of PQQ, a choline salt from Example 2 as a 1.4 choline salt of PQQ, a choline salt from Example 3 as a dicholine salt of PQQ, a choline salt from Example 4 as a 2.4 choline salt of PQQ, and a choline salt from Example 5 as a tricholine salt of PQQ.

These salts were dissolved up to saturation at room temperature of 23 to 28° C., and these solutions each were diluted by 20 times or 400 times with a phosphate buffer having a pH of 7.5. For the diluted solutions each, an analysis of the ultraviolet-visible absorption spectra was carried out using a HITACHI U-2000 spectrometer. The solubility of pyrroloquinoline was determined by the absorbance (in a range of 0 to 2) at 450 nm.

TABLE 1

| | Choline Salt of PQQ | Solvent | Relative Ratio | mmol/L |
|---|---|---|---|---|
| Comparative Example 1 | Disodium Salt of PQQ | Water | 1 | 7.99 |
| Comparative Example 2 | Disodium Salt of PQQ | Ethanol | 0.03 | 0.23 |
| Example 6 | Monocholine Salt of PQQ | Water | 0.24 | 1.94 |
| Example 7 | Monocholine Salt of PQQ | Ethanol | 0.06 | 0.52 |
| Example 8 | 1.4 choline Salt of PQQ | Water | 1.01 | 8.06 |
| Example 9 | 1.4 choline Salt of PQQ | Ethanol | 5.56 | 44.42 |
| Example 10 | Dicholine Salt of PQQ | Water | 11.8 | 94 |
| Example 11 | Dicholine Salt of PQQ | Ethanol | 13.9 | 111 |
| Example 12 | 2.4 choline Salt of PQQ | Water | 21.5 or more | 171 or more |
| Example 13 | 2.4 choline Salt of PQQ | Ethanol | 21.5 or more | 171 or more |
| Example 14 | Tricholine Salt of PQQ | Water | 21.5 or more | 171 or more |
| Example 15 | Tricholine Salt of PQQ | Ethanol | 21.5 or more | 171 or more |

As shown in Table 1, as the ratio of choline to PQQ increased, the solubility of the choline salt of PQQ in water and ethanol increased. Especially when the molar ratio of PQQ to choline is 1:1.9 to 1:3, the choline salt has a high solubility, and can be dissolved in water or ethanol by 10 times compared to the sodium salt. Furthermore, the sodium salt is almost insoluble in ethanol, but can be made to be dissolved as is the case in water by converting into the choline salt.

Examples 16 to 18 and Comparative Example 3

Mixing Test

A predetermined amount of choline chloride was added to 0.1 g of a disodium salt of PQQ. To this mixture were added 8 ml of ethanol, and the absorbance at 450 nm was measured for the supernatant liquid. Taking Comparative Example 3 without choline chloride as a standard, the amounts of PQQ dissolved relative to the standard were calculated and the results are shown in the following Table 2.

TABLE 2

| | Disodium Salt of PQQ (g) | Choline Chloride (g) | Amount Dissolved |
|---|---|---|---|
| Comparative Example 3 | 0.1 | 0 | 1 |
| Example 16 | 0.1 | 0.01 | 1.4 |
| Example 17 | 0.1 | 0.1 | 3.9 |
| Example 18 | 0.1 | 0.2 | 5.8 |

Mixing with choline chloride increased the solubility in alcohol, resulting in effective compositions.

Example 19

Preparation of the Reduced Form

Equal portions of an aqueous solution of 0.5 mM dicholine salt of PQQ obtained in Example 3 and an aqueous 10 mM ascorbic acid solution were mixed in a 2 ml vessel. This mixture was diluted by ten times with water, and the ultraviolet-visible absorption spectrum (at 220 to 700 nm) was measured for the diluted solution. A new peak appeared near 300 nm, which showed that the reduction as described in Bull. Chem. Soc. Jpn., Vol. 59, pp. 1911-1914 (1986) was in progress. The conversion was 100% at 70° C. for 15 hours and 63% at room temperature for 20 hours. In this way, the dicholine salt of PQQ can be converted to the corresponding choline salt in the reduced form.

Example 20

Preparation of Triethanolamine Salt of PQQ

A 0.47 g aliquot of PQQ in the free form obtained in Example 1 were suspended in 20 ml of water. To the suspension was added triethanolamine from Wako Pure Chemical Industries, Ltd. to adjust the pH of the mixture to 3.7 while observing with a pH meter. As the reaction proceeded, the suspension turned into a solution, and this solution was stirred overnight. The solvent was removed from the solution obtained in a 300 ml eggplant-shaped flask using an evaporator, and the residue was washed with isopropanol, and dried under reduced pressure to yield 0.79 g of a solid. This solid was analyzed by LC and ion chromatography, and the results showed that a salt wherein a molar ratio of PQQ and triethanolamine is 1:2 was formed.

The invention claimed is:

1. A choline salt of oxidized pyrroloquinoline quinone of formula (3):

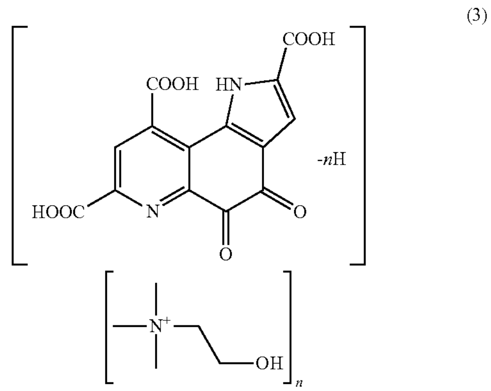

wherein:

n is two to three.

2. A choline salt of reduced pyrroloquinoline quinone of formula (4):

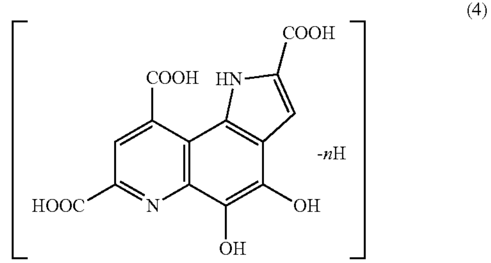

-continued

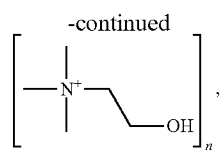

wherein:

n is two to three.

3. A composition, comprising the choline salt of oxidized pyrroloquinoline quinone of claim 1 and a reducing agent selected from the group consisting of ascorbic acid, cystein, borohydride, NADPH, hydrosulfite and hydrazine.

4. The composition of claim 3, wherein a weight ratio of the reducing agent to the choline salt of oxidized pyrroloquinoline quinone is in a range of 0.01 to 100.

5. A composition, comprising the ammonium salt of oxidized pyrroloquinoline quinone of claim 1 and an ammonium salt of reduced pyrroloquinoline quinone of formula (4):

(4)

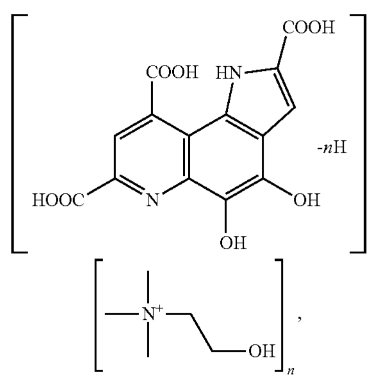

wherein n is two to three.

6. A method for producing the choline salt of the oxidized pyrroloquinoline quinone of formula (3) of claim 1, the method comprising:

subjecting an alkali metal salt of the oxidized pyrroloquinoline quinone represented by formula (5) to acidic conditions, to form an acidified pyrroloquinoline quinone:

(5)

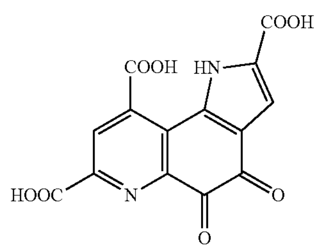

and mixing the acidified pyrroloquinoline quinone with an ammonium hydroxide, wherein the ammonium hydroxide is choline hydroxide, and the salt produced is a choline salt of the oxidized pyrroloquinoline quinone.

7. A method for producing the choline salt of the reduced pyrroloquinoline quinone represented of formula (4) of claim 2, the method comprising:

subjecting an alkali metal salt of the reduced pyrroloquinoline quinone represented by formula (6) to acidic conditions, to form an acidified pyrroloquinoline quinone:

(6)

and mixing the acidified pyrroloquinoline quinone with an ammonium hydroxide, wherein the ammonium hydroxide is choline hydroxide, and the salt produced is a choline salt of the reduced pyrroloquinoline quinone.

* * * * *